United States Patent
Ueki

(10) Patent No.: US 6,328,761 B1
(45) Date of Patent: Dec. 11, 2001

(54) DISPOSABLE BODY WARMER FOR USE IN FOOTWEAR

(75) Inventor: Akio Ueki, Osaka (JP)

(73) Assignee: Kiribai Chemical Co., Ltd., Osaka (JP)

( * ) Notice: Subject to any disclaimer, the term of this patent is extended or adjusted under 35 U.S.C. 154(b) by 1054 days.

(21) Appl. No.: 08/858,564

(22) Filed: May 19, 1997

Related U.S. Application Data

(63) Continuation of application No. 08/290,774, filed on Aug. 24, 1994, now abandoned.

(51) Int. Cl.[7] .................................................. A43B 7/02
(52) U.S. Cl. ........................... 607/111; 2/239; 36/2.6
(58) Field of Search ..................... 607/108–112, 111; 36/59 R, 2.6; 525/27; 521/76; 428/402.21; 21/239

(56) References Cited

U.S. PATENT DOCUMENTS

| | | | |
|---|---|---|---|
| 3,802,951 | * | 4/1974 | Mitchell ................. 36/59 R |
| 3,828,792 | * | 8/1974 | Valenta .................. 128/619 |
| 4,012,855 | * | 3/1977 | Gardner ................. 36/59 R |
| 4,069,515 | * | 1/1978 | Swallow ................. 36/59 R |
| 4,249,319 |   | 2/1981 | Yoshida . |
| 4,434,565 | * | 3/1984 | Haley .................... 36/59 R |
| 4,628,072 | * | 12/1986 | Shiraki et al. ............ 525/27 |
| 4,753,241 | * | 6/1988 | Brannigan ............... 607/111 |
| 5,282,326 | * | 2/1994 | Schroer .................. 36/44 |
| 5,470,893 | * | 11/1995 | Sinclair-Day ............ 523/205 |

FOREIGN PATENT DOCUMENTS

| | | | |
|---|---|---|---|
| 0 526 637 |   | 2/1993 | (EP) . |
| 57-3637 |   | 1/1982 | (JP) . |
| 3220864 | * | 9/1988 | (JP) .................. 607/111 |
| 63-309254 |   | 12/1988 | (JP) . |
| 2-131760 |   | 5/1990 | (JP) . |
| 2-149218 |   | 12/1990 | (JP) . |
| 5-20722 |   | 3/1993 | (JP) . |
| 5176951 | * | 7/1993 | (JP) .................. 607/111 |

* cited by examiner

Primary Examiner—Linda C. M. Dvorak
Assistant Examiner—David M. Ruddy
(74) Attorney, Agent, or Firm—Armstrong, Westerman, Hattori, McLeland & Naughton, LLP

(57) ABSTRACT

A body warmer for use in footwear is disclosed which is prevented from slipping in footwear and is capable of warming a desired portion accurately, and which includes an exothermic composition capable of generating heat in the presence of air, an air-permeable bag accommodating the composition, and an air-tight bag sealingly enveloping the air-permeable bag, the air-permeable bag being formed with a non-slip layer in at least a portion thereof.

13 Claims, 1 Drawing Sheet

DISPOSABLE BODY WARMER FOR USE IN FOOTWEAR

This application is a continuation of application Ser. No. 08/290,774 filed Aug. 24, 1994, now abandoned.

TECHNICAL FIELD

The present invention relates to a disposable body warmer for use in footwear (hereinafter referred to as "body warmer" for simplicity). More particularly, it relates to a body warmer which is prevented from slipping in footwear and is capable of warming a desired portion accurately.

BACKGROUND ART

Hitherto, it has been known a disposable body warmer of the type wherein an exothermic composition which generates heat in the presence of air is accommodated within an air-permeable bag (inner bag) and this inner bag is enveloped with an air-impermeable bag (outer bag).

Body warmers of such type include, as well as one for warming limbs and waist portions, a thin and small-sized one which has been proposed for warming of the sole of a foot.

However, where such a conventional body warmer adapted to warm the sole of a foot is used in a shoe, there arises a problem that it tends to slip in the shoe and hence cannot warm a desired portion accurately.

To solve this problem, there is proposed a body warmer of the type in which its inner bag is provided with an adhesive layer on one side thereof and which is adapted to be stuck to a desired portion of the sole of a foot with an intervening sock or stocking, or to be stuck directly to the sole of a shoe.

This type of body warmer, however, has problems that it is difficult for the warmer to be disposed in position for use and to be released after use and that socks or stockings or the soles of shoes are likely to be soiled because of the adhesive remaining on the portion from which the body warmer has been released.

There are additional problems that in the course of determining a location to which the body warmer is to be stuck in a shoe by groping, the body warmer might be stuck to an undesired portion, and that the adhesive layer might be stuck to the sole of a shoe too tightly because of the weight of user applied on his or her foot and, hence, the base fabric of the shoe would be damaged when the body warmer is released therefrom after use.

In view of the foregoing circumstances, it is an object of the present invention to provide a body warmer which is prevented from slipping in footwear and is capable of warming a desired portion accurately.

DISCLOSURE OF THE INVENTION

A body warmer according to the present invention is characterized by comprising an exothermic composition capable of generating heat in the presence of air, the composition being accommodated in an air-permeable bag, and an air-impermeable bag sealingly enveloping the air-permeable bag, the air-permeable bag being formed with a non-slip layer in at least a portion thereof.

BEST MODE FOR CARRYING OUT THE INVENTION

Figure 1:
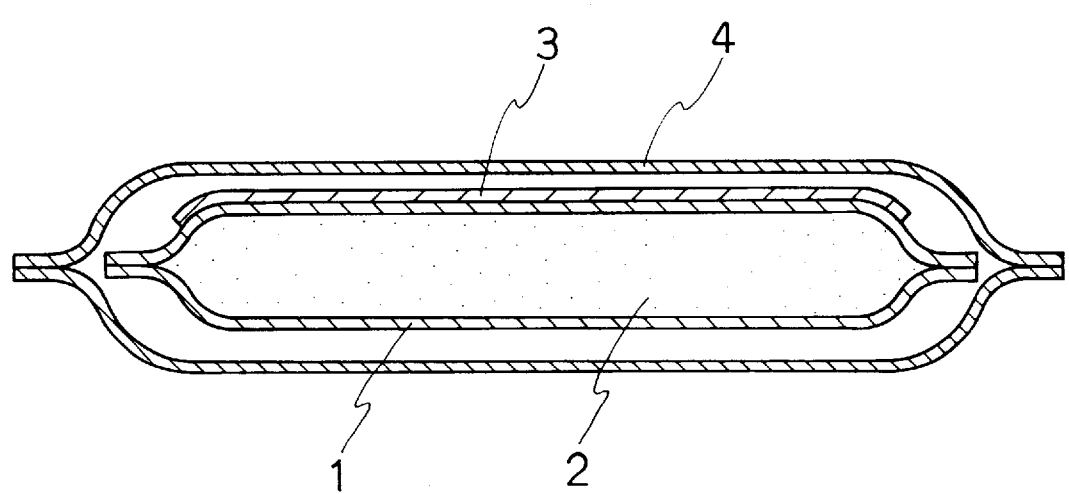
FIG. 1 is an explanatory section of one embodiment of a body warmer according to the present invention.

A body warmer according to the present invention will now be described in detail with reference to the attached drawing.

Referring to FIG. 1, numeral 1 denotes a flat air-permeable bag having a multiplicity of permeable pores or micropores. The inner bag 1 has an air-permeable surface in at least a portion thereof. In other words, one side (the lower side in FIG. 1) of the inner bag 1 might constitute an air-permeable surface and the other side might constitute an air-impermeable surface. Further, both sides might constitute an air-permeable surface. Otherwise, one side of the inner bag 1 might comprise the air-permeable surface in a portion thereof and an air-impermeable surface in the rest.

The air-permeability of the inner bag 1 is not particularly limited. Nevertheless, each permeable pore should be sized so as not to permit the content of the bag to escape therethrough to the outside, for example, about 0.5 mm or smaller. Further, the range of the quantity of air flowing through the inner bag 1 is not particularly limited in the present invention as far as it allows the exothermic composition to generate heat, but is usually 50 to 5000 g/m²·day, preferably 400 to 1800 g/m²·day, particularly preferably 500 to 1600 g/m²·day on the basis of the measurement according to a cup method provided in JIS Z 0208.

Though materials for the inner bag 1 are not limited in the present invention, it is preferable to use such materials that are soft and strong, not nappy, and have stable quality, applicability for heat sealing. Usable concrete examples are, for example, plastic-like or rubber-like flexible thermoplastic sheet or film comprising polyurethane, polypropylene or polyethylene, or modifications thereof; and a single layer or complex layer of non woven fabric, polyvinyl chloride, polyester or polystyrene.

It should be noted that, for the surface of the inner bag on which a non-slip layer 3 to be described later is to be formed, there can advantageously be used a laminate of about 10 to about 100 µm thickness comprising a film of a polyester such as polyethylene terephthalate or of a polypropylene and a woven or nonwoven fabric or paper. Where this laminate is used, the outer surface thereof should be formed of the nonwoven fabric or the like and the non-slip layer 3 is formed thereon.

As a method for controlling air-permeability of an air-permeable surface of an inner bag 1, there is a method wherein appropriate heat welding treatment is applied to a sheet or film on which minute continuous pores are formed. Concretely speaking, the air-permeability can be controlled, for example, by uniformly distributing or entirely applying heat welding agent which is heated appropriately on a sheet or film having uniform continuous pores of 1 to 50 µm in diameter. Otherwise, the air-permeability of a sheet or film might be adjusted by punching the sheet or film.

Alternatively, the air-permeability of the inner bag can be controlled by laminating a resin film having permeable micropores on a non-woven fabric.

The size of the inner bag 1 is not particularly limited in the present invention. There can be used any inner bag of the size within a range such as to allow insertion thereof into a shoe. Further, the bag 1 might be shaped circular, elliptic or rectangular. Preferably, it is tongue- or horseshoe-shaped to fit the shape of the sole of a foot.

As the exothermic composition 2 to be sealed within the inner bag 1, there can be used one comprising metal powder such as of iron (preferably the metal powder is treated with sulfur or a sulfur-containing compound), activated carbon, water, a water-retaining material (powdery wood, vermiculite, diatomaceous earth, pearlite, silica gel, alumina, water-absorptive resin or the like), common salt and the like. Such ingredients of the composition are not limitative in the present invention.

The present invention is characterized by the provision of the non-slip layer 3 in at least a portion of the inner bag 3. The non-slip layer 3 might be formed over the entire surface of one side of the inner bag 1 or over portions thereof as exhibiting one of various patterns such as a dotted pattern or striped pattern so as to enhance the non-slip effects.

Specific examples of the non-slip layer 3 are as follows:

(1) On a surface of the material of inner bag 1 is applied a solution or dispersion of resin or elastomer or a plastisol either uniformly or as drawing a pattern, followed by drying.

Examples of the resin or elastomer to be used include soft vinyl chloride resin, natural rubber, styrene-butadiene rubber, isoprene rubber, chloroprene rubber, urethane rubber.

(2) On a surface of the material of inner bag 1 is applied a resin material of hot melt type either uniformly or as drawing a pattern by hot melt coating method.

Examples of the resin material of hot melt type include hot melt adhesives each comprising, as a major ingredient thereof, ethylene-vinyl acetate copolymer, hydrolysate of ethylene-vinyl acetate copolymer, ethylene-acrylic acid copolymer, ethylene-acrylic acid ester copolymer, polyamide resin, polyester resin or the like.

(3) A heat-meltable resin is extrusion-laminated on a surface of the material of inner bag 1.

Preferably, the heat-meltable resin exhibits good tackiness, and examples of such a preferred heat-meltable resin include ethylene-methyl methacrylate copolymer (EMMA).

(4) A surface of the material of inner bag 1 is applied or impregnated with a foamable resin composition either uniformly or as drawing a pattern, followed by foaming the resin composition to form a foamed layer of the resin.

(5) A synthetic resin film is laminated on a surface of the material of inner bag 1.

One example of the foamable resin composition is a polyurethane resin composition for use with a foaming agent such as water or a neutral liquid of low melting point. Another example of the foamable resin composition is a mixture of a binder resin and capsules each containing a core of a resin such as an acrylic resin (for example, a thermosetting acrylic resin such as vinylidene chloride-acrylonitrile copolymer) and a foaming agent (volatile solvent such as isobutane) contained in the core. Applying this mixture on a surface of inner bag 1 and foaming the same will give a layer having rough surface.

In applying each resin material onto the inner bag 1 for drawing a pattern as described above, a gravure coater or the like can be used.

In addition, where there is used the hot melt adhesive, soft vinyl chloride resin or the like, if such material in a particulate form is uniformly dispersed on a surface of the material of the inner bag 1 and fixed thereon by heating, a multiplicity of projections can be formed on the surface of the inner bag 1.

Placing the body warmer in footwear so as to bring such a non-slip layer 3 into contact with an inner surface (on which the sole of a foot is to be placed) of the footwear will prevent the body warmer to be shifted and allows desired portions to be warmed.

The inner bag 1 is sealingly enveloped by an air-tight or air-impermeable outer bag 4 made of a non-porous film of polyethylene, polypropylene or the like.

As has been described, the body warmer of the present invention is provided with the non-slip layer formed on a surface of the inner bag and, hence, the body warmer is able to warm desired portions accurately without fear of slipping and shifting thereof during use.

Industrial Applicability

The body warmer of the present invention is capable of warming a desired portion of a body accurately and is particularly useful as a body warmer for use in footwear.

What is claimed is:

1. A body warmer comprising an exothermic composition capable of generating heat in the presence of air, the composition being accommodated in an air-permeable bag, and an air-tight bag sealingly enveloping the air-permeable bag, the air-permeable bag being formed with a non-slip layer in at least a portion thereof, the non-slip layer being an outermost layer of the air-permeable bag, wherein the non-slip layer comprises a resin, elastomer or a plastisol, and is formed by applying a solution or dispersion of a resin or elastomer or a plastisol onto a surface of the air-permeable bag, followed by drying.

2. A body warmer comprising an exothermic composition capable of generating heat in the presence of air, the composition being accommodated in an air-permeable bag, and an air-tight bag sealingly enveloping the air-permeable bag, the air-permeable bag being formed with a non-slip layer in at least a portion thereof, the non-slip layer being an outermost layer of the air-permeable bag, wherein the non-slip layer comprises a hot melt resin material, and is formed by applying a hot melt resin material onto a surface of the air-permeable bag according to a hot melt coating method.

3. A body warmer comprising an exothermic composition capable of generating heat in the presence of air, the composition being accommodated in an air-permeable bag, and an air-tight bag sealingly enveloping the air-permeable bag, the air-permeable bag being formed with a non-slip layer in at least a portion thereof, the non-slip layer being an outermost layer of the air-permeable bag, wherein the non-slip layer comprises a heat-meltable resin, and is formed by extrusion laminating a heat-meltable resin on a surface of the air-permeable bag.

4. A body warmer comprising an exothermic composition capable of generating heat in the presence of air, the composition being accommodated in an air-permeable bag, and an air-tight bag sealingly enveloping the air-permeable bag, the air-permeable bag being formed with a non-slip layer in at least a portion thereof, the non-slip layer being an outermost layer of the air-permeable bag, wherein the non-slip layer comprises a foamed resin layer and is formed by applying or impregnating a foamable resin composition onto or into a surface of the air-permeable bag, followed by foaming.

5. A body warmer comprising an exothermic composition capable of generating heat in the presence of air, the composition being accommodated in an air-permeable bag, and an air-tight bag sealingly enveloping the air-permeable bag, the air-permeable bag being formed with a non-slip layer in at least a portion thereof, the non-slip layer being an outermost layer of the air-permeable bag, wherein the non-slip layer comprises a foamed synthetic resin, and is formed by laminating a foamed synthetic resin film on a surface of the air-permeable bag.

6. The body warmer of any one of claims 1 to 5, wherein a surface of the air-permeable bag on which the non-slip layer is formed is made of a film of polyester, nylon, polyethylene or polypropylene; and wherein the non-slip layer is formed on the film.

7. The body warmer of any one of claims 1 to 5, wherein a surface of the air-permeable bag on which the non-slip layer is formed is made of a laminated layer including a film of polyester, polyethylene or polypropylene and a layer of a woven fabric, nonwoven fabric or paper; and wherein the non-slip layer is formed on an outer layer of the air-permeable bag, the outer layer being formed of the layer of the woven fabric, nonwoven fabric or paper.

8. The body warmer of any one of claims 1 to 5, wherein the non-slip layer is formed in a pattern.

9. The body warmer according to claim 1, wherein the resin or elastomer is selected from the group consisting of soft vinyl chloride resin, natural rubber, styrene-butadiene rubber, isoprene rubber, chloroprene rubber and urethane rubber.

10. The body warmer according to claim 2, wherein the hot melt resin material is a hot melt adhesive comprising a member selected from the group consisting of ethylene-vinyl acetate copolymer, hydrolysate of ethylene-vinyl acetate copolymer, ethylene acrylic acid copolymer, ethylene-acrylic acid ester copolymer, polyamide resin and polyester resin.

11. The body warmer according to claim 3, wherein the heat-meltable resin is ethylene-methyl methacrylate copolymer.

12. The body warmer according to claim 4, wherein the foamable resin composition is a polyurethane resin composition.

13. The body warmer according to claim 4, wherein the foamable resin composition comprises a binder and capsules each containing a core of thermosetting acrylic resin and a foaming agent.

* * * * *